United States Patent [19]

Atwood et al.

[11] 4,014,612
[45] Mar. 29, 1977

[54] PHOTOMETRIC MEASURING APPARATUS

[75] Inventors: John G. Atwood, Redding; Hamilton W. Marshall, Jr., Ridgefield; Charles F. Demey, II, West Redding; Wilson P. Ralston, Stamford, all of Conn.

[73] Assignee: The Perkin-Elmer Corporation, Norwalk, Conn.

[22] Filed: Aug. 22, 1974

[21] Appl. No.: 499,855

[52] U.S. Cl. .................................. 356/88; 356/95; 356/206
[51] Int. Cl.² ........................................ G01J 3/42
[58] Field of Search ............... 356/88, 89, 93, 94, 356/95, 206; 250/211 J

[56] References Cited

UNITED STATES PATENTS

| | | | |
|---|---|---|---|
| 3,022,704 | 2/1962 | Cary | 356/94 |
| 3,449,050 | 6/1969 | Keahl | 356/89 |
| 3,506,358 | 4/1970 | Baba et al. | 356/206 |
| 3,588,253 | 6/1971 | Wittmann | 356/93 |
| 3,606,547 | 9/1971 | Iwahashi | 356/95 |
| 3,671,751 | 6/1972 | Kortge et al. | 250/211 J |
| 3,723,008 | 3/1973 | Fukuda et al. | 356/88 |
| 3,843,258 | 10/1974 | Shupe | 356/88 |
| 3,910,701 | 10/1975 | Henderson et al. | 356/201 |

*Primary Examiner*—Vincent P. McGraw
*Attorney, Agent, or Firm*—S. A. Giarratana; F. L. Masselle; J. M. O'Meara

[57] ABSTRACT

A highly stable and sensitive photometric apparatus is obtained by combining a sensitive, stable, unchopped, dual-beam optical photometer with an accurate electronic sensing circuit. The circuit includes PIN silicon diode detectors on which the two beams of the photometer are imaged. One beam is a reference to detect light source variations and the other a signal beam passing through the sample cell of the photometer. The PIN diode outputs are inputs to parametric amplifiers. The amplifier outputs are then provided to log taking means which take the logarithms of the two signals and then take the difference of the two logarithms to provide a final output proportional to absorbtion in the cell.

6 Claims, 5 Drawing Figures

PHOTOMETRIC MEASURING APPARATUS

BACKGROUND OF THE INVENTION

This invention relates to measuring apparatus in general and more particularly to an improved photometer, detector and amplifier arrangement for use in automatic analysis apparatus.

Photometric analytical apparatus which measure quantities such as the absorbance of light by certain fluids and the like are well known in the art. An improved type of such apparatus is that disclosed in copending application of John G. Atwood et al Ser. No. 499,602 filed Aug. 22, 1974. This application has now been abandoned and a continuation application Ser. No. 594,951 filed July 10, 1975 has been filed on the subject matter thereof. In the photometer disclosed therein, reacting serum samples are provided to a flow cell through which a beam of light is passed. At the same time, another portion of the beam which is used as a reference is passed through an additional optical path. For the light output of the beam after passing through the reacting mixture to be of any value in determining absorbance in the mixture, means must be provided for detecting the light level and for amplifying the detected level to a voltage value which is useful. Various means of providing such an output have been developed. In general, each of these comprises a photodetector along with stages of amplification. To obtain the proper type of output, the amplification must also include amplifiers having logarithmic input or feedback in order to provide an output which is proportional to absorbance. Although many such systems have been developed, all suffer from a certain lack of accuracy and/or a low signal-to-noise ratio.

For example, it has been common practice in the prior art that most sensitive and stable photometers for measuring small changes in absorbance of samples, achieve sensitivity and stability through the use of the double beam and optical modulation system in which a beam of spectrally filtered radiation or portions of the beam from a suitable source of selected wavelengths is alternately directed along a path through the sample and a reference path by passing the sample. The beams sample and reference are the combined on a single detector to produce a periodically time-varying signal. In large part this is a requirement due to the limitations of photodetectors previously used. In these prior art systems, the periodic signal is then demodulated to generate a signal in proportion to the difference between absorbance in the sample and reference paths. In the very best examples of this prior art approach to sensitive photometry, the least detectable change in absorbance is about $5 \times 10^{-4}$ absorbance unit.

In view of the foregoing state of the art, it is the object of the present invention to provide an improved photometer, detector, amplifier arrangement which provides increased accuracy along with improved signal-to-noise ratio.

SUMMARY OF THE INVENTION

The present invention resides in the combination of the photometer of a copending application of John G. Atwood et al, Serial No. 499,617 filed August 22, 1974 with a circuit which permits optimum utilization of the characteristics of the optical system of that photometer.

The photometer of the present invention is highly stable and has very high sensitivity in that extremely small absorbance changes are detectable in a fluid sample at a particular wave length of interest. It also exhibits improved sensitivity of measurement of the rate of change of absorbance of a fluid sample over a short period of time, as is desired in kinetic analysis using catalyzed reactions by enzymes. Furthermore, the invention broadens the dynamic range of absorbance over which a small change in absorbance can be measured, while all this is accomplished with small sample volumes, e.g., 100 microliters or less. The photometer of the present invention does not require the modulation (or beam chopping) found in the prior art but still achieves a sensitivity which is an order of magnitude better than that found in prior art photometers, i.e., it can regularly measure absorbance changes in fluid samples as small as $5 \times 10^{-5}$ units. Features of the photometer which permit achieving this result are a high stability optical design in an unmodulated double beam arrangement and an accurate electronic circuit.

The detectors which measure the intensity of the reference and sample beams in the photometer are silicon PIN diode detectors the output signals of which are provided as inputs to parametric amplifiers. Surprisingly, this combination results in a signal accuracy far exceeding that which can be expected from the individual components. The parametric amplifier outputs are then coupled to operational amplifiers having logarithmic elements in their feedback paths and the logarithm of the respective output signals is thereby provided. The two logs so developed are then subtracted in a further operational amplifier to provide a final output which is proportional to the absorbance in the sample cell. Accuracy is further insured by enclosing at least the logarithmic amplifiers within an enclosure the temperature of which is regulated between predetermined limits.

The silicon PIN diode detectors are particularly suitable because the response over their active area is quite constant. Furthermore, their response is not particularly dependent on their recent history of illumination and is repeatable at any given temperature. However, PIN diode detectors of this type have an extremely small active area requiring an optical system such as that described herein which can accurately position the beams of light on these sensitive areas. Thus, through the coaction of the optical portion and the electronic portion of the system, an extremely accurate photometer exhibiting better sensitivity and repeatability than was heretofore possible is obtained.

In addition, the sample cell itself is thermally isolated within a cavity and maintained at a predetermined temperature. Because of its thermal isolation, the sample, which is preheated on its way through the photometer cell, and the cell remain at a constant temperature throughout the measurement cycle. The sample is heated by being passed through a metal block the temperature of which is regulated by a control system including a thermistor and a heat pump.

DETAILED DESCRPITION OF THE PREFERRED EMBODIMENT

Figure 1:
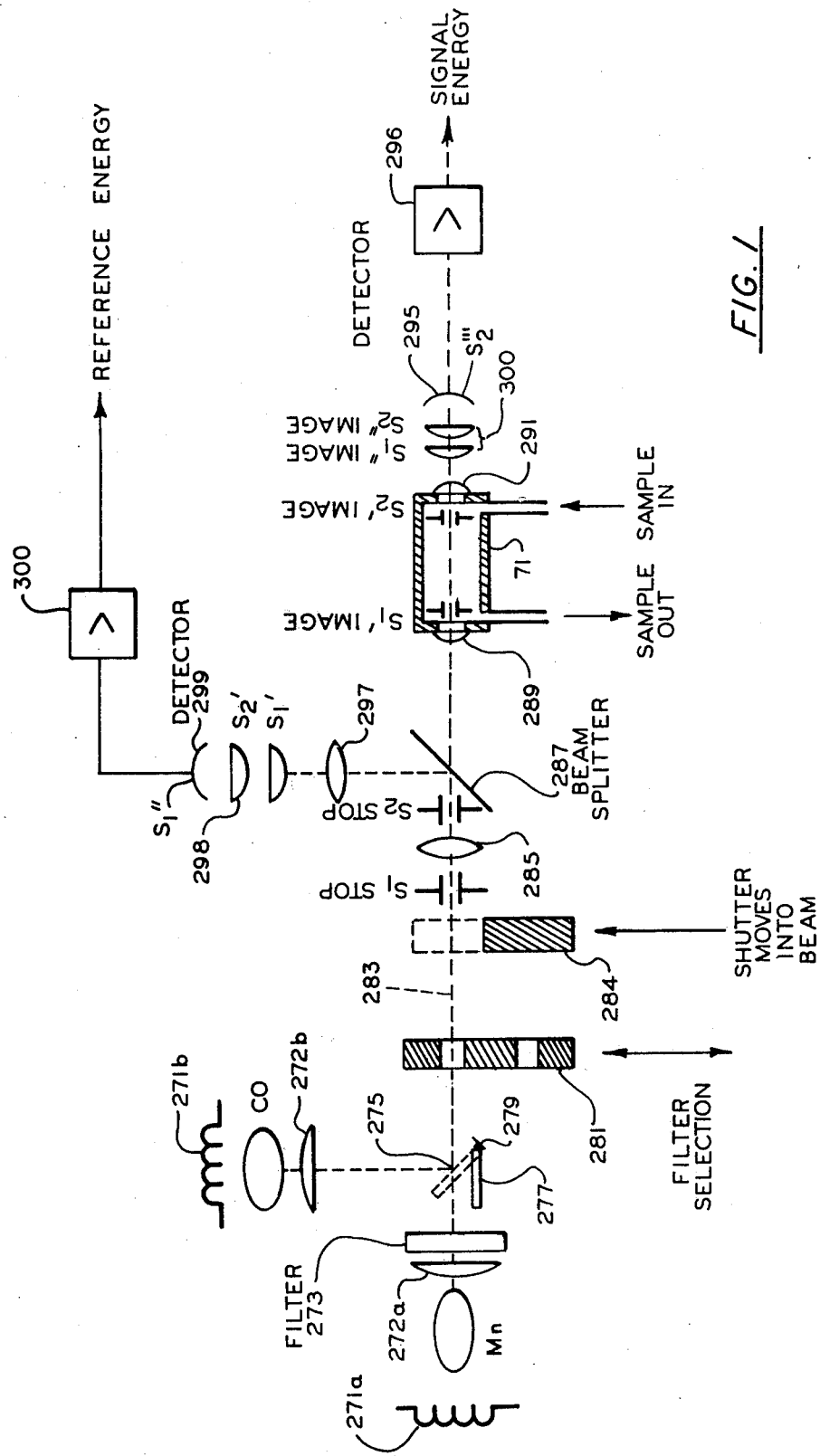
FIG. 1 is an optical mechanical schematic diagram of the photometer of the present invention.

Referring first to FIG. 1, the photometer includes a light source capable of emitting light of two predetermined wavelength bands. In the illustrated embodiment, the source includes two hollow cathode lamps with one being a manganese lamp 271a emitting light at approximately 404nm and the other being a cobalt lamp 271b emitting light at approximately 340nm. Since the wavelengths emitted are those of the atoms of the lamps' cathodes, these wavelengths are extremely stable and repeatable contributing to the stability of the photometer. Lenses 272a and 272b are provided respectively in front of the lamps 271a and 271b to form beams of light. A 404 nm filter 273 maybe disposed in front of the lens 272a. The two light paths formed by lenses 272a and 272b intersect at a point 275 on a mirror 277 in one rotatable position thereof about an axis 279. Which of the lamps is used as the light source is determined by the test being run. Depending on the test selection, a control signal will cause the mirror to be rotated to the position in solid lines for light at 404 nm or the position shown on dotted lines for light at 340 nm. In conjunction therewith, a movable filter 281 is positioned to pass only a frequency band containing the selected wavelengths. The selected wavelengths of light then travel along the optical axis 283 toward a photometric sample cell 71. It is important to define the etendu of the light beam along the optical axis 283 so that it is possible to split that beam into a signal path and a reference path, each of which will have known and controlled throughputs of light flux. In so defining the etendu of the beam along the optical axis 283, it is essential that the light source have an area of essentially uniform brightness and that the image of this area of uniform brightness overfills the first stop upon which it is imaged so that the full cross-section of the beam is of the same uniform brightness in spite of small mechanical motions of the source. The etendu is defined through the use of a field stop $S_1$ and an aperture stop $S_2$ with a lens 285 therebetween. The light beam prior to encountering the stops $S_1$ and $S_2$ passes a shutter 284 which is controlled by an appropriate timing signal to maintain the shutter is normally closed and is opened only for a predetermined period when the absorbance measurement is being made for reasons described below.

The beam having a defined etendu is then directed to a beamsplitter 287 of the coated type which preserves uniformity of illumination in both light paths. The beamsplitter 287 is coated so as to transmit approximately 90% of the beam and reflect the remaining 10%. Thus, the two beams formed thereby are each of lower intensity than the original beam, but both are of uniform illumination across their respective cross-sections. The transmitted portion of the beam, i.e., the portion containing 90% of the energy, enters the cell 71, first passing through a lens 289. The lens 285 images the field stop $S_1$ at $S_1'$ near the entrance to the cell, with the lens 289 imaging the stop $S_2$ at $S_2'$ near the exit of the cell. These lens 285 and 289 are shown only as examples and it will be recognized by those skilled in the art that any equivalent lens arrangement which will so image the stops may be used. The purpose of this imaging is to insure that the light path is kept away from the sides of the cell, and further that the boundaries of the beams are well defined, so that small mechanical motions of the parts may occur without the beams hitting either the walls of the cell, or the margins of any of the optical parts. This makes the throughput of light flux in the beam stable with respect to small mechanical or optical distrubances. A further lens 291 is provided at the exit end of the cell 71 to image the stops $S_1$ and $S_2$ respectively at $S_1''$ and $S_2''$ a condenser lens arrangement 300 which includes two lenses and images the stop $S_2$ at $S_2$ on a detector 295. It is essential that the lenses of the condenser arrangement 300 be able to encompass largest possible input angle, so that they collect a maximum of scattered light. Although the beam is well defined travelling through the cell 71 the liquid therein may scatter the beam to some degree and the improved results obtained with the photometer system are at least partially due to this ability to collect nearly all such scattered light. Furthermore, it is essential that the lenses 300 image the light well within the boundaries of the active area of the detector 295 so that all of the output from the cell is measured in spite of small mechanical motions of the optical parts which cause the beam to move.

Light in the reflective path from beamsplitter 287 is directed through a lens 297 and a pair of condenser lenses 298. Lens 297 images the field stop $S_1$ and $S_1'$ on the first lens and the stop $S_2$ at $S_2'$ on the second lens. The second lens images the stop $S_1$ at $S_1''$ on a second detector 299. Again it is essential that all of the beam be imaged within the sensitive area of the detector 299.

As will become more evident below, the output of the detector 299, which is reference detector, is used to cancel from the output of the detector 295, which is the signal detector, any output variations resulting from variations at the illumination sources 271a and 271b. Any variation occurring before the beam-splitter 287 will thus be cancelled out. The signals from the detectors as illustrated are amplified in respective amplifiers 296 and 294 and then processed in a manner to be described below. The shutter 284 is kept closed i.e., in a position to block passage of light along the optical axis 283 except during a measurement cycle. Therefore, when samples are being transferred, the shutter remains closed to prevent any inaccuracies due to the response time of the detectors 295 and 299 because light from both the sample and reference beams is applied to both of these detectors at the same time. Were the shutter left open the light of the reference beam would be on the reference detector 299 continuously whereas the detector 295 could have a lag in responding to a sample transferred to the cell. Under such circumstances, errors could result, because of the difference in the illumination history of the two detectors.

If these teachings are faithfully carried out, then the only phenomena that will significantly affect the ratio of the signals detected from the two beams is a change in absorbance of the sample.

In spite of all precaution, small mechanical and optical distrubances will occur, some of which may cau̇e the images to move or change size on the detector's sensitive areas. Therefore, it is advantageous that the detectors have uniform response to light over their active area. Further, since the response of detectors to light is dependent upon their temperature, it is important that the two detectors be at the same temperature and that this temperature not change during the measurement.

Figure 2:
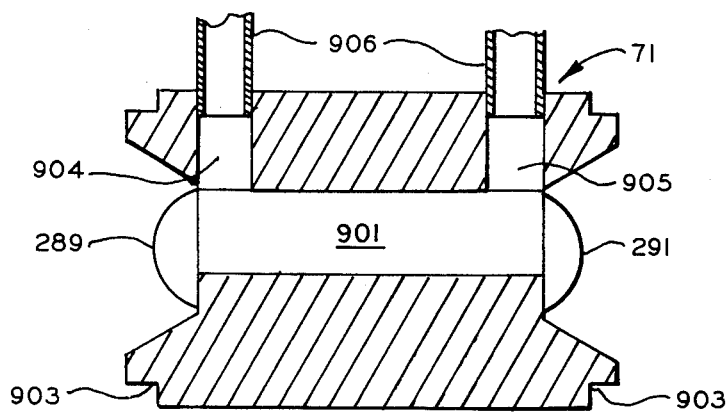
FIG. 2 is a more detailed cross-section of the sample cell of FIG. 1.
Figure 3:
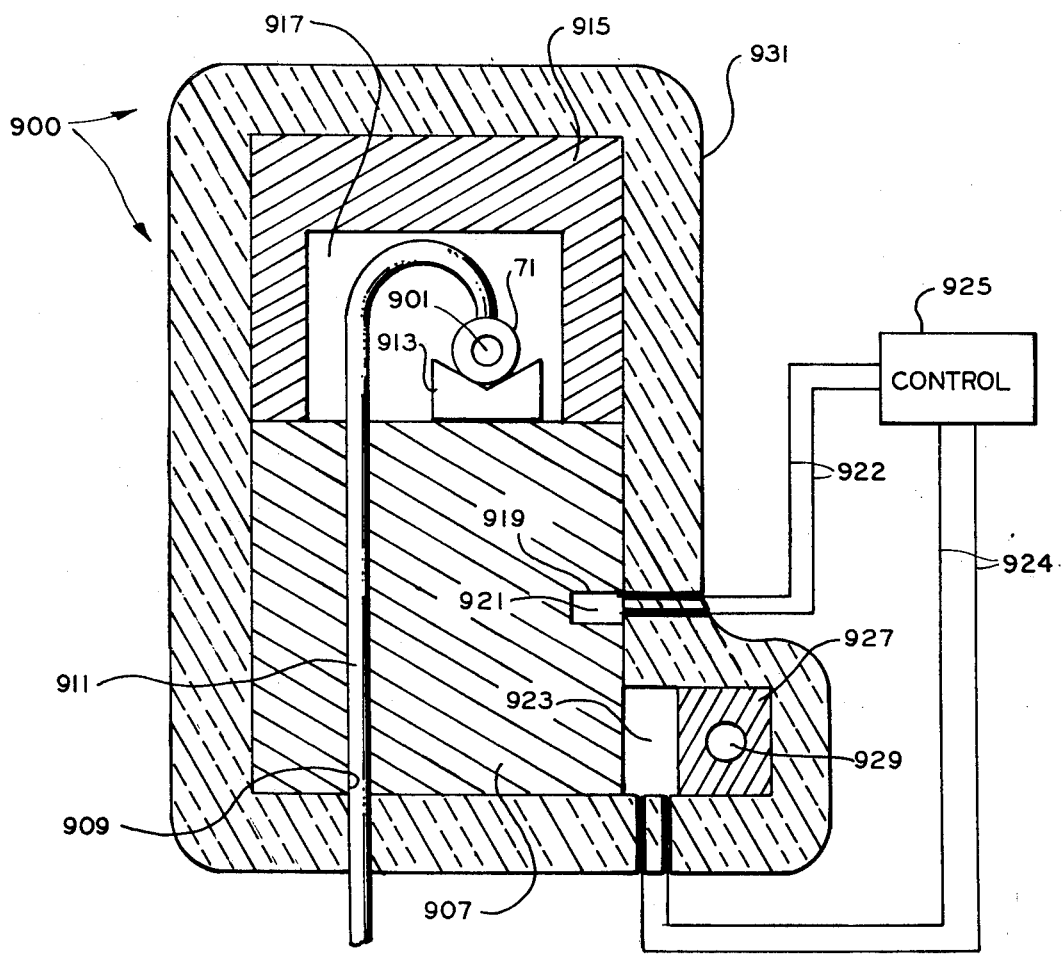
FIG. 3 is a cross-sectional view of means which may be used to control sample temperature.

A more deailed illustration of photometer cell 71 is shown in FIG. 2, where the cell itself is made of silver and defines a sight passage 901 in which the sample rests during analysis. The end of passage 901 are closed by lens-shaped members 289 and 291 which form part of the optical system as already explained. Cell 71 is essentially cylindrical in its external configuration and is provided with cutouts 903 for nesting in a plastic block as will be described presently openings 904 and 905 are provided into the cell 71 in flow communication with the respective ends of passage 901, for enabling the introduction and removal of a sample. The transfer of a sample to cell 71 may be effected by means of a transfer system described and claimed in a copending application of John G. Atwood et al for U.S. Patent, Ser. No. 499,618, filed Aug. 22, 1974 and assigned to the same assignee as the present invention. Inserted into each of the openings 904 and 905 is a stainless steel nipple 906. While it is important that the sample be maintained at a particular temperature during measurement, it is more important that the temperature remain constant during analysis. For example, it may be sufficient if the temperature of the sample in the cell is within 0.2° c of the desired temperature, 30° c, for a particular enzyme determination; however, the temperature during the analysis period should not vary more than 0.01° c. FIG. 3 shows a heat exchanger assembly 900 for bringing the sample to a desired temperature and maintaining it at that temperature. This assembly 900 includes a thermostated base block 907 made of aluminum and containing a tubular passage 909 within which is inserted a stainless tube 911. The upper end of the tube 911 is connected through Tygon tubing to the sample cell nipple 906 at the inlet end of the sight passage 901. Cell 71 nests on a plastic V block 913, having good thermal insulation properties and being supported on top of the block 907. A cover 915, also of aluminum and having a cavity 917 therein, is placed over the block 907 and bolted in place. A recess 919 in block 907 accomodates the insertion of a thermistor 921. Attached to the side of block 907 below thermistor 921 is a heat pump 923 which preferably takes the form of a Peltier device such as Borg Warner part no. 903-17. Leads 922 from thermistor 921 are connected to a control device 925 which provides outputs over leads 924 to operate the heat pump 923 in conventional fashion. On the opposite side of the heat pump 923 with respect to block 907 is a further metal block 927 having a passage 929 through which water is circulated to remove heat from the heat pump when it is operating in a cooling mode. The heat exchanger assembly 900 is surrounded with insulating material 931 which may comprise, for example, plastic foam insulation. In operation, heat pump 923 adjusts the temperature of the aluminum block 907 to the desired value. This results in the temperature of cavity 917 being approximately at the desired value, i.e., it is close enough to this value to provide accurate results. However, as noted above, the sample must not change its temperature during measurement. The use of the silver cell 71 and its thermal isolation from block 907 by means of the Tygon tubing connected between tubes 911 and nipples 906, as well as the plastic V block 913, assures the requisite temperature invariance. The high thermal conductivity of the silver causes it to reach an equilibriumtemperature with the sample very quickly.

Heat pump 923 proportionally changes the temperature of the aluminum block slightly, e.g., as the temperature of the block drops a small amount, the heat pump will increase its heat flow to bring it up to the set value. The temperature of the block 907 does not vary much but even a small variation would be sufficient to effect the accuracy of photometric analysis if sample cell 71 were not isolated by the plastic V block 913. Furthermore, the detectors 295 and 299 which are located within the cavity 917 and will also be maintained at essentially constant temperature.

Figure 4:
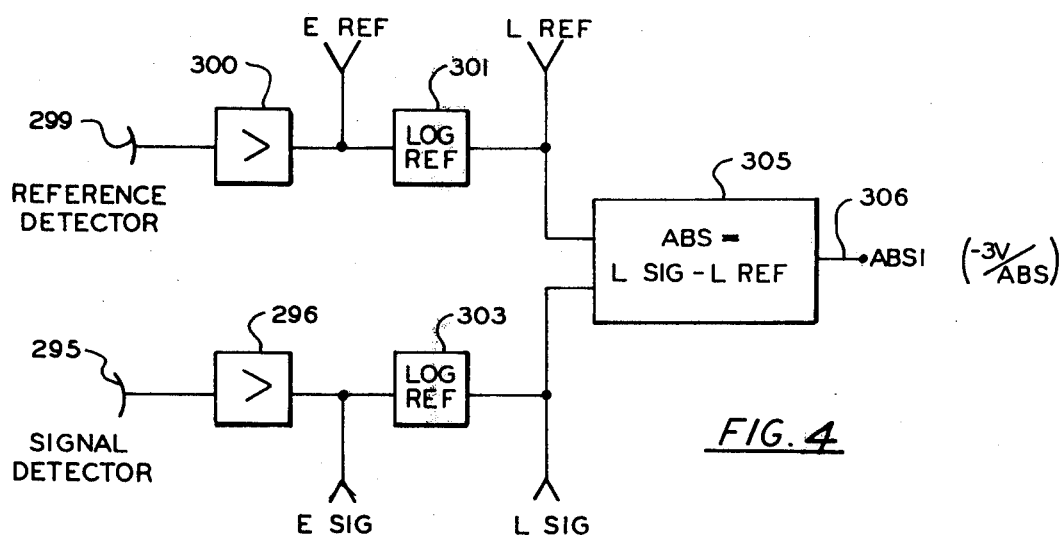
FIG. 4 is a block diagram of the detector and amplifier circuit of the present invention.

A basic block diagram from the detector outputs is shown in FIG. 4 where silicon PIN diodes are utilized as the detectors 299 and 295 from which the outputs connected to amplifier stages 300 and 296 respectively. A test point E REF and E SIG respectively is provided for each of the amplifier outputs which are also connected to circuit means for deriving signals logarithmically proportional to each of the amplifier outputs and for determining the difference between the logarithmic signals so derived. Included in this circuit means are circuit 301 which takes the log of the reference detectors output and circuit 303 which takes the log of the signal detector output. These two logarithmic signals are provided as the separate inputs to an analog subtractor 305 and as outputs at the test points designated L REF and L SIG. The absorbance is calculated in the analog subtractor 305 where the logarithm of the reference detector output is subtracted from the logarithm of the signal detector output with the difference therebetween being provided on a line 306.

Figure 5:
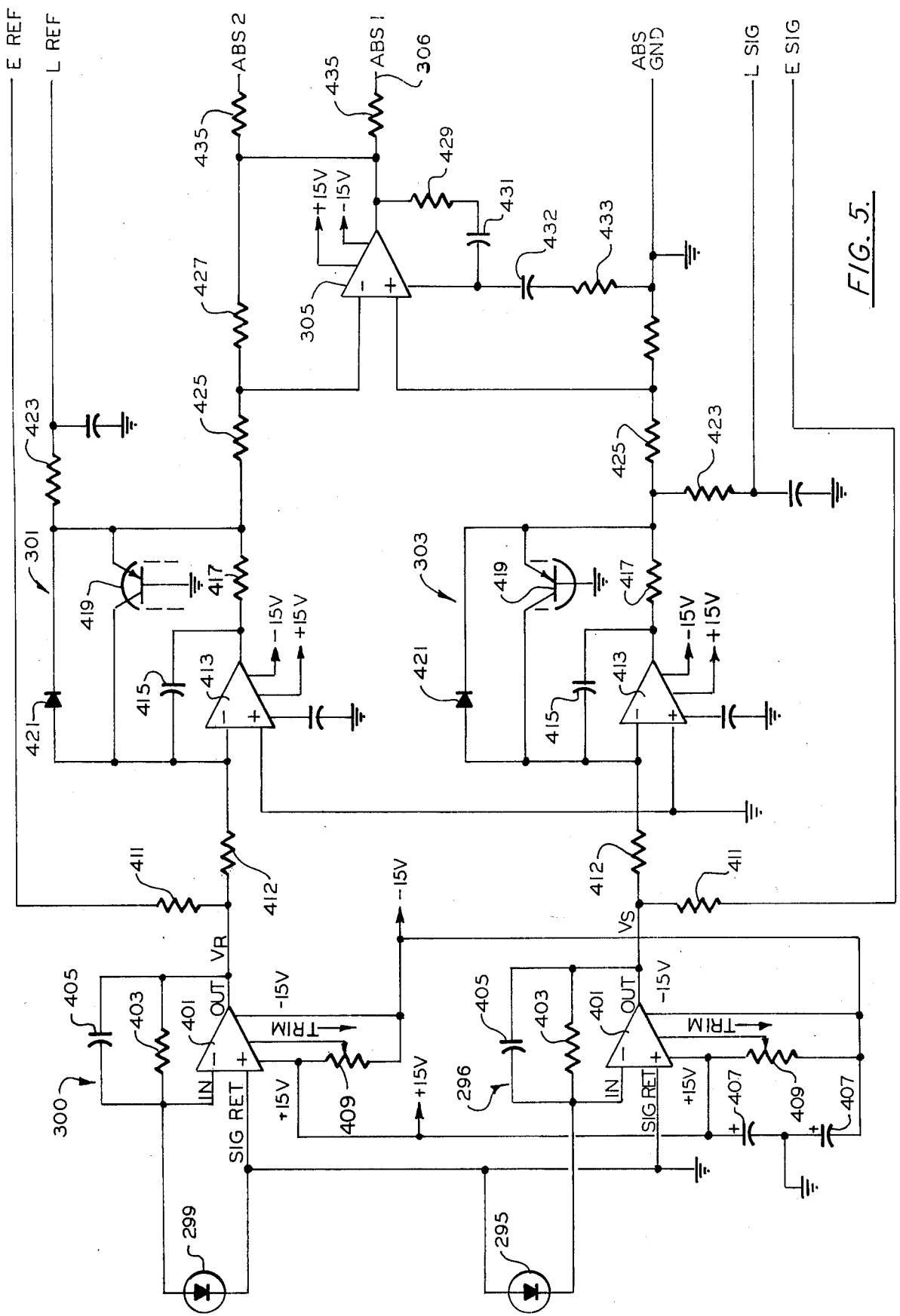
FIG. 5 is a schematic diagram of the circuit of FIG. 4.

A more detailed schematic drawing of the detector output circuits is shown in FIG. 5 where outputs from the 295 and 299 are connected as inputs to the amplifiers 296 and 300, respectively. The detectors must be silicon PIN photodiodes such as those manufactured by Motorola designated as MDR 510. These detectors have a sensitive area with uniform response, are not particularly dependent on recent history of illumination and are characterized by repeatable response at a given temperature. Each of the amplifiers 296 and 300 comprises a parametric amplifier 401 with negative feedback through a feedback resistance 403. In parallel with each feedback resistance, typically 1,000 megohms for amplifier 296 and 3,000 megohms for amplifier 300, are capacitors 405 which may be 5 picofarads each. Each of the amplifiers is provided with positive and negative supply voltages typically at $+$ and $-15$ V. Decoupling capacitors 407 are provided between the positive and negative voltage supplies and ground in conventional fashion. Typically, these may be 6.8 micro farad capacitors. Associated with each amplifier is also a trim potentiometer 409 with its wiper coupled in the usual way to an appropriate amplifier input. As shown, trim potentiometers 409 are coupled across the positive and negative supply. The amplifiers themselves may be type 301 J manufactured by Analog Devices.

The outputs of the amplifiers 296 and 300 are provided through respective resistors 411 to the appropriate test points. They are also provided through resistors 413 to the logarithmic circuits 301 and 303, respectively. Each of the logarithmic circuits include an operational amplifier 413 having its non-inverted input grounded and the input signal provided to its inverting input. Typically these amplifiers may be National Semi-Conductor LM308AH amplifiers. Input resistors between the amplifiers 296 and 300 and the logarithmic stages, i.e., input resistors 412, may be 100 k ohms.

A logarithmic function is obtained through appropriate feedback circuits. Thus, the output of each of the amplifiers 413 is first fed back directly to its inverting input through a capacitor 415 and then fed back through a resistor 417 and parallel legs having a transistor 419 with its base grounded and a diode 421 respectively therein. Typical components are 75 picofarads for capacitors 415 each transistor 419 is onehalf of a 2N4023 device; and resistors 417 may be 5 k ohms. The signals developed at the output of the logarithmic circuits are taken off after the resistors 414 to the test points through resistors 423 in conventional fashion. These two signals are also connected through resistors 425, which are a matched pair of resistors to an operational amplifier amplifier connected as the subtractor 305. The signal detector output from the logarithmic circuit 303 is provided to the non-inverting input and the reference detector output from the logarithmic circuit 301 to the inverting input of the subtractor 305 which may be, for example, a Precision Monolithic 725C amplifier. Amplifier 305 has a resistor 427 in its feedback path to establish appropriate scaling.

Appropriate compensating circuits comprising resistor 429, capacitor 431, capacitor 432 and resistor 433 are provided in conventional fashion. The output of the substractor 305 is then taken off through a resistor 435 as the absorbance signal on line 306. A second output through a second resistor 435 is provided to a meter, if desired. Resistor 427 may be a 49.9K resistor and resistors 435 may be 47 ohms resistors.

Thus, an improved photometer detector and amplifying arrangement has been shown. Although a specific embodiment has been illustrated and described, it will be obvious to those skilled in the art that various modifications may be made without departing from the spirit of the invention which is intended to be limited solely by the appended claims.

What is claimed is:

1. In photometric apparatus for the type wherein absorbance through a sample cell in one of two radiation paths is determined by directing light from a source of predetermined wavelength contemporaneously along both paths, the improvement comprising:
   a first PIN diode disposed at the end of the path with the sample cell to detect intensity of radiation thereat;
   a second PIN diode disposed at the end of the oher path to detect intensity of radiation thereat;
   a field stop, a lens, and an aperture stop sequentially aligned along an axis to receive light from the source and to pass a beam of uniform intensity over the cross-sectional area thereof;
   means for proportionally distributing said beam to the paths;
   means for focusing light from said beam distributing means to symmetrically image said field and aperture stops substantially at the entrance and exit respectively of the sample cell;
   means for focusing light that passes from the sample cell to symmetrically image said aperture stop wholly on the sensitive area of said first PIN diode;
   means for focusing light from said beam distributing means to symmetrically image one of said field and aperture stops wholly on the sensitive area of said second PIN diode;
   first and second parametric amplifiers separately disposed to receive the outputs from said first and second PIN diodes respectively; and
   circuit means for deriving signals logarithmically proportional to the output from each said parametric amplifier and for determining the difference between said logarithmic signals.

2. The combination of claim 1 further including means for maintaining said PIN diodes at substantially equal and constant temperatures.

3. The combination of claim 1 wherein said circuit means includes first and second logarithmic amplifiers and a differential amplifier having the inputs thereof separately connected to the respective outputs from said logarithmic amplifiers.

4. The combination of claim 3 wherein said logarithmic amplifiers and said differential amplifier each include an operational amplifier 5. The combination of claim 1 further including shutter means for simultaneously occluding light from the source along both paths.

6. The combination of claim 1 further including means for maintaining said PIN diodes at substantially equal and constant temperatures, along with shutter means for simultaneously occluding light from the source along both paths; and wherein said circuit means includes first and second logarithmic amplifiers and a differential amplifier having the inputs thereof separately connected to the respective outputs from said logarithmic amplifiers, said logarithmic amplifiers and said differential amplifier each including an operational amplifier.

* * * * *